United States Patent [19]
Sheehan et al.

[11] Patent Number: 5,533,085
[45] Date of Patent: Jul. 2, 1996

[54] AUTOMATIC INDEXING OF CINE-ANGIOGRAMS

[75] Inventors: Florence H. Sheehan, Mercer Island; Gregory L. Zick, Kirkland; Hain-Ching H. Liu, Seattle, all of Wash.

[73] Assignee: University of Washington, Seattle, Wash.

[21] Appl. No.: 395,034

[22] Filed: Feb. 27, 1995

[51] Int. Cl.⁶ .................................................. H65G 1/60
[52] U.S. Cl. ........................................ 378/95; 364/413.13
[58] Field of Search .................................. 378/95, 98.11, 378/98.12; 364/413.13

[56] References Cited

U.S. PATENT DOCUMENTS 4,689,670  8/1987  Okazaki ................................. 378/98.5

*Primary Examiner*—David P. Porta
*Assistant Examiner*—David Vernon Bruce
*Attorney, Agent, or Firm*—Ronald M. Anderson

[57] ABSTRACT

A method and system for identifying end systole and end diastole frames within an angiography sequence. A plurality of images produced during an angiography sequence are digitized, producing digital image data in which gray scale values for each of the pixels in the images are represented. The digital image data are input to a computer (48) to determine the frames in which the coronary arteries are most visible. The coronary arteries are made visible in the images by injecting a radio-opaque contrast substance into the arteries. The frames that occur a end diastole are preferred for diagnostic analysis because the arteries are distended, spread apart from each other, and moving very slowly. To identify such frames for further analysis, the total length of edges within a centered window covering approximately one-fourth of each image is determined. The edges represent spatial transitions between relatively light and dark areas in the image that occur across the borders of the coronary arteries. At end diastole during the cardiac cycle, the total length of the coronary arteries within the window is substantially less than at end systole, when the heart has contracted to a minimum volume. Frames in which a local maximum total edge length is observed thus depict the arteries at end systole. Similarly, frames having a local minimum total edge length show the arteries at end diastole. Either a spatial method or a discrete cosine transform (DCT) method is used for determining the total edge length in each frame.

36 Claims, 9 Drawing Sheets

AUTOMATIC INDEXING OF CINE-ANGIOGRAMS

FIELD OF THE INVENTION

The present invention generally pertains to a method and system for processing digitized imaging data, and more specifically, for processing digital data derived from images produced during an angiography sequence, as a function of edges detected within the images.

BACKGROUND OF THE INVENTION

Coronary angiography is an important procedure in the diagnosis of medical problems associated with the coronary arteries that supply blood to the heart. During this procedure, the coronary arteries are imaged to enable a medical practitioner to observe any blood circulation problems that may affect the heart.

A radio-opaque contrast substance injected into the coronary arteries during the angiography procedure causes the arteries to appear as bright lines against a relatively darker background. Where a restriction (stenosis) has occurred in a coronary artery, the artery will appear to be pinched, i.e., it will have a smaller cross-sectional thickness at the location of the restriction. Since the heart is three-dimensional, a stenosis in a coronary artery may not be evident from certain viewing angles. It is typically necessary to produce at least five angiography sequences, each at a different projection angle relative to the heart, to ensure that all portions of the coronary arterial system are visually presented for accurate medical diagnosis.

During each of the angiography sequences in which the radio-opaque contrast substance is injected into one of the coronary arteries, from 150 to 250 consecutive frames are recorded with a cine camera and/or a video camera, or in a digital format. Each sequence records from five to 15 cardiac cycles or heart beats. During each beat, the heart ventricles fill with blood during diastole, reaching their maximum volume at end diastole. The heart muscle contracts during systole, and the ventricles reach their minimum volume at end systole. Most of the filling of the coronary arteries with blood takes place during diastole, because the coronary arteries pass through the heart muscle, and the pressure exerted by the contracting muscle during systole tends to impede blood flow through the arteries. During the imaging sequence, the injected radio-opaque contrast substance can be seen to fill the coronary artery and then to gradually clear from the artery as fresh blood, which does not contain the radio-opaque contrast substance, enters the arteries.

When making a diagnostic analysis of the images in accord with clinical procedures, a physician will either estimate the severity of coronary artery stenosis based on a visual examination of the images, or perform a quantitative analysis of the artery lumen dimension at the point of maximum stenosis and in the adjacent normal anew segment(s) disposed above and/or below the stenosis. Commercially available software programs designed to partially automate the measurements of these artery dimensions may be used. For either analysis, a physician will typically view all of the frames in a sequence and then repetitively view some of the frames that appear to include the best images of the coronary anew at end diastole. The frames of greatest interest are those that show the stenotic segment and the adjacent normal segment(s) clearly, free of overlying branch vessels or other structures, with minimal foreshortening, without blurring due to motion, and when the anew is filled with the radio-opaque contrast substance. This condition occurs most frequently at end diastole, because at that point in the cardiac cycle, the increased volume of the heart separates the branches from each other, there are few motion artifacts as the heart pauses to change direction from moving outwardly to moving inwardly, and the artery is not compressed by muscle contraction. Occasionally, the stenotic artery segment may be most clearly visualized in the frame following end systole, which is another time at which there are few motion artifacts as the heart pauses to change direction from moving inwardly to moving outwardly. The physician will thus likely select a preferred image showing the coronary anew at end diastole or possibly, at end systole, for further analysis.

Conventionally, the physician only performs diagnostic analysis on selected images from the one sequence that best shows the stenotic artery segment. Alternatively, the same steps may be again manually implemented by the physician to select one or more preferred frames in other angiography sequences.

In some hospitals, the quantitative analysis may be performed by medical staff who are not physicians, such as radiology technicians. Also, the analysis may not be performed until some time following the coronary angiography procedure, for example, when the physician has completed the examination and is dictating a report for the patient's files.

The time required for the physician or technician to review the frames in an angiography sequence to select those images for further analysis varies, depending on the quality of the images, the skill of the medical practitioner, and the criteria applied in making the selection. In some cases, only a few minutes will be required to manually select specific images from an angiography sequence. However, even the relatively short time required to manually make the selection can be significant, particularly if the patient is waiting to undergo further angiography sequences, pending a decision that the severity of coronary stenosis is sufficient to warrant a change in treatment, or that the treatment applied in a cardiac catheterization facility has adequately reduced the stenosis.

Another problem that arises in connection with the current practice of manually selecting the preferred frames in a sequence of angiogram images for analysis relates to the problem of integrating the angiogram image data with other information, such as the patient's history, and of maintaining and searching the image data at a later time. Image data produced during an angiography procedure are sometimes digitized to facilitate automated analysis and then are indexed and stored. However, the files in which digitized image data for a complete sequence of angiogram images are stored can be quite large. Even when compression techniques such as those developed by the Joint Photographic Expert Group (IPEG) or by the Motion Picture Expert Group (MPEG) are used to reduce the file sizes, the amount of digital image data produced by digitizing a complete angiography sequence can quickly fill available digital storage resources. Ideally, only the selected frames from each sequence should be stored, along with indexing information that indicates the parameters associated with the selected frames. A patient identifier, the date of the angiography procedure, the sequence number(s) from which the selected frames are derived, the frame number of the selected frames, and the digital image data for the selected frames should provide a sufficient record to support any subsequent diagnosis made from the selected frames. The conventional approach in which angiography images are manually reviewed and selected for further analysis does not readily permit such a record to be produced and maintained.

Based on the preceding remarks, it will be evident that at least an initial selection of the angiography images that will be used for further analysis and diagnosis should be automated. By automating the selection process, the time required to start the diagnosis can be greatly reduced. In addition, the automated process should improve the quality of the selection process by minimizing subjective criteria that may incorrectly influence the choice of a frame in an angiography sequence. If the selection process is thus automated, indexing of the selected frames for storage with a patient's medical history is easily implemented.

SUMMARY OF THE INVENTION

In accordance with the present invention, a method is defined for selecting specific images from a plurality of angiography images. The specific images depict coronary arteries at an end systole and at an end diastole of a cardiac cycle during which the coronary arteries are maximally visible against a background of the images. In the method, digital data corresponding to the plurality of angiography images are provided; the digital data indicate gray scale values for a plurality of pixels within the images. Next, at least a portion of each image is divided into blocks of pixels. Each block comprises a plurality of rows and columns of pixels. Using the digital data for pixels in the rows and columns of a block, the number of edges disposed within the block is determined, based on changes in the gray scale values that occur across each edge. For each image, the total length of the edges within an area of the image in which the blocks are disposed is determined by adding the edges in all of the blocks processed. Based upon temporal changes in the total length of the edges in each image, images that depict the coronary arteries at end systole and at end diastole are selected. An image that depicts the coronary arteries at end systole has a substantially greater total length than an image that depicts the coronary arteries at end diastole.

In one embodiment of the method, the digital data are in a compressed form, so that gray scale values in the images are indicated using discrete cosine transform (DCT) components. The steps of determining the number of edges in each block and of selecting the images include determining a DCT for each of the blocks using the DCT components of the digital data.

In another embodiment, the step of determining the number of edges in the block comprises the steps of comparing differences between the gray scale values for selected pixels in each row and in each column of the block, to a threshold, and comparing the gray scale values to each other. As a function of substantial differences in the gray scale values, the number of edges in each row and column of the block is thus determined. The threshold is determined so as to ensure that there is a substantial difference in the total length of the edges in the images depicting the coronary arteries at the end systole and the end diastole.

Preferably, the portion of the images divided into blocks comprises a window that is substantially smaller in area than each image. The window is disposed within the images at a position that encompasses a substantial portion of the coronary arteries. The method further calls for repeating the first five steps discussed above, with the window disposed at each of a plurality of different positions. A preferred position for the window is selected based upon differences of the total length of the edges when the window is disposed at the plurality of different positions. The preferred position is selected by comparing differences in the total length of the edges in images depicting the coronary arteries at end systole and end diastole, determined with the window at each of the plurality of different positions. The position of the window that yields a greatest difference in the total length of the edges in the images is selected as the preferred position.

Another aspect of the present invention is directed to a system for automatically selecting specific images from a plurality of images produced during a coronary angiography procedure. The specific images that are selected depict coronary arteries during a defined portion of a cardiac cycle. Included in the system is a digitizer that converts visual images into digital data. The digital data represent gray scale values for a plurality of picture elements that comprise the images produced during the angiography procedure. The system also includes a computer coupled to the digitizer to receive the digital data. The computer includes a central processing unit (CPU) that executes machine instructions. These machine instructions comprise a program for processing the digital data to select the specific images. Non-volatile storage is provided for the digital data, and a memory is provided for use in storing the machine instructions for execution by the CPU. When executing the machine instructions, the CPU comprises means for selecting the digital data corresponding to blocks of the picture elements in each image. For each image, the blocks represent the digital data for at least a portion of the image that is disposed at a position common to each image. The picture elements of each block comprise a plurality of rows and columns. Execution of the machine instructions by the CPU also comprises means for processing the digital data for each of the blocks to determine a total length of the edges disposed within each image, and means for selecting the specific images depicting the defined portion of the cardiac cycle based on temporal differences in the total length of the edges disposed within each image.

Other functions implemented by the components of this system are generally consistent with the steps of the method discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

Figure 7:
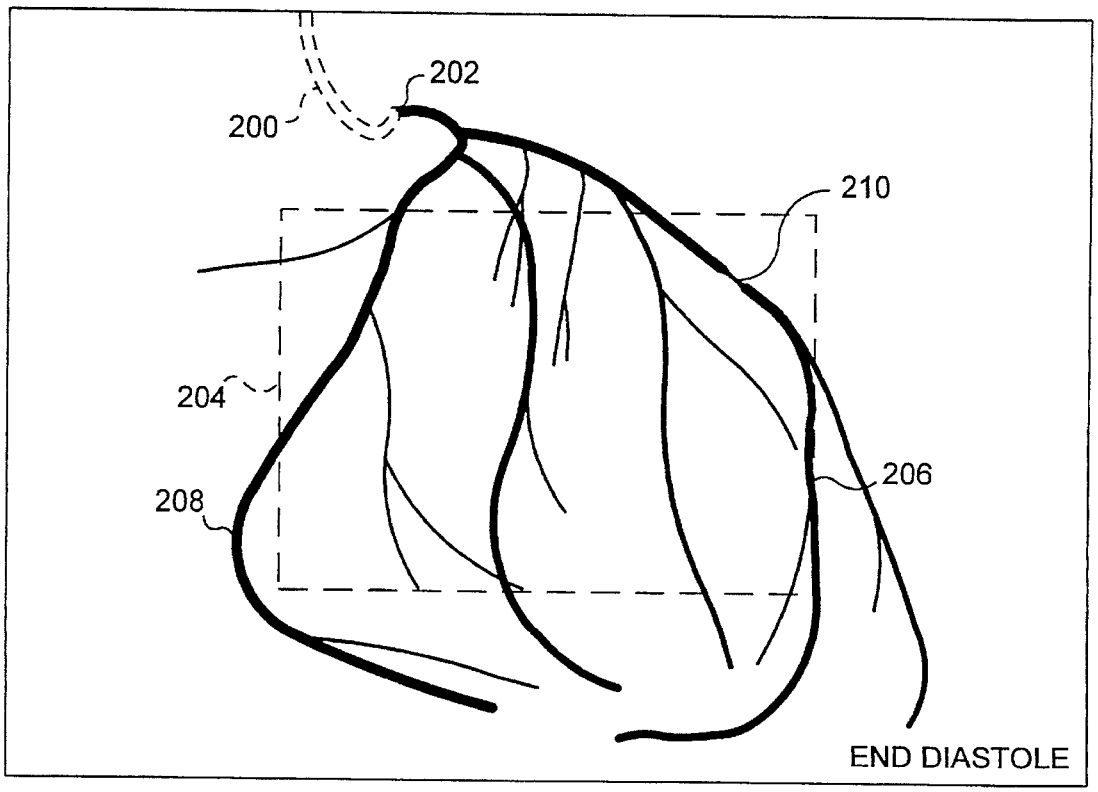
Figure 8:
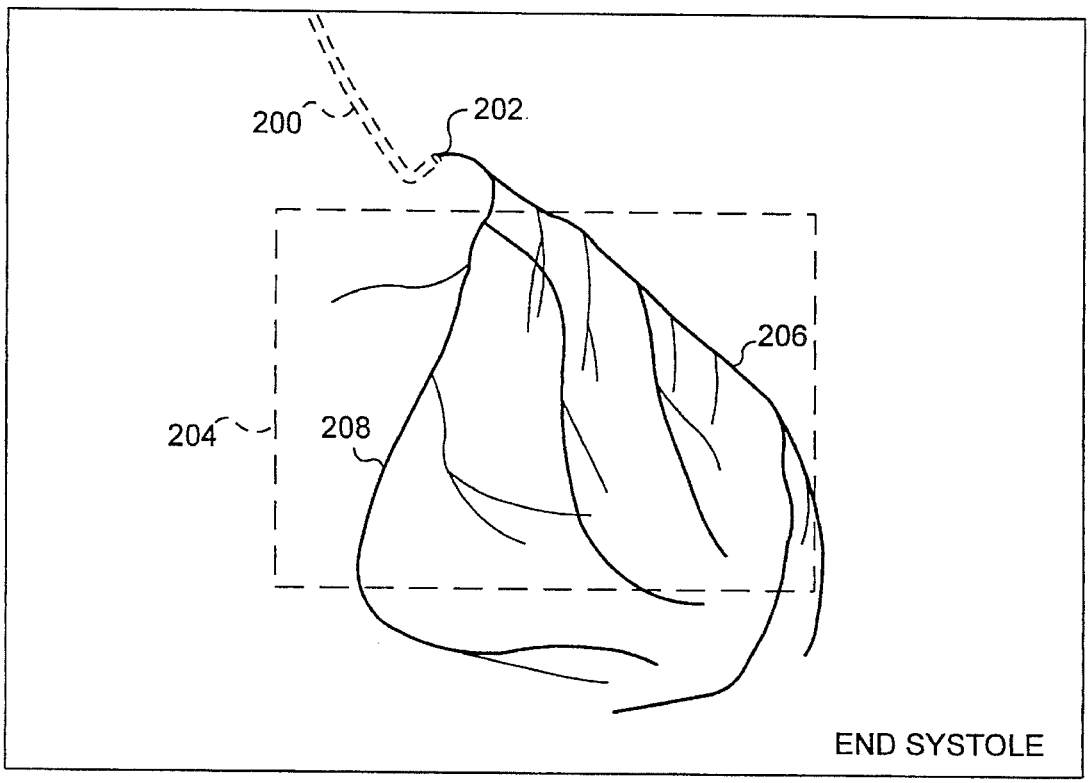
Figure 9:
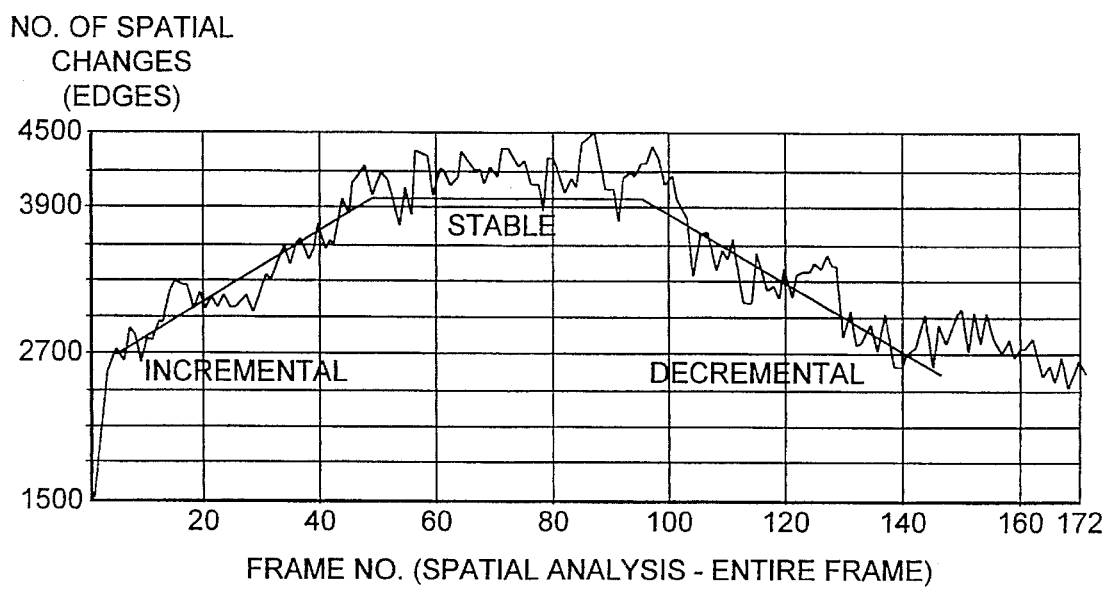
Figure 10:
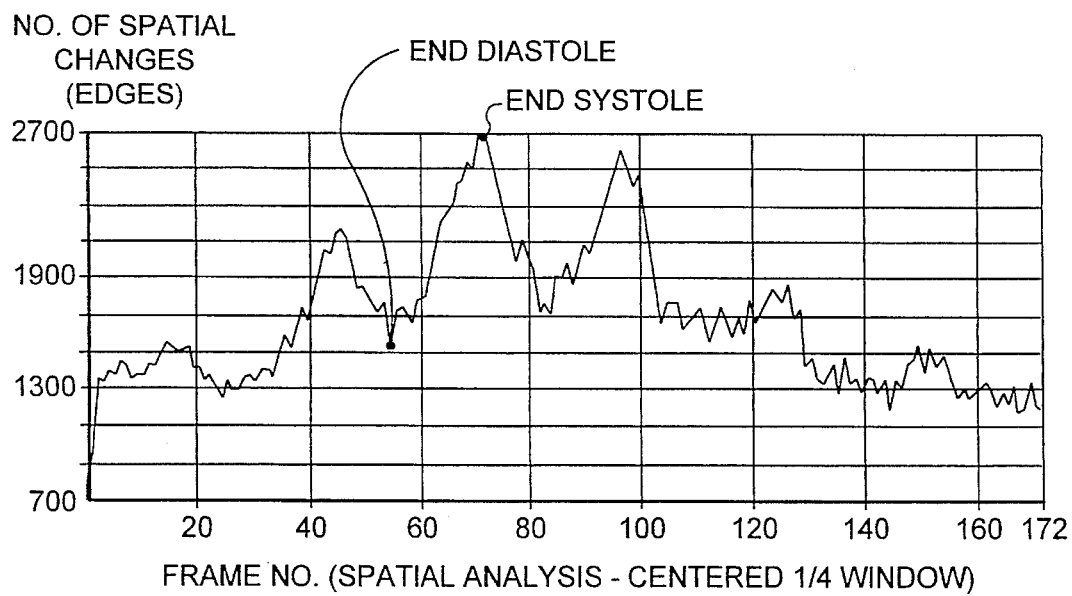
Figure 11:
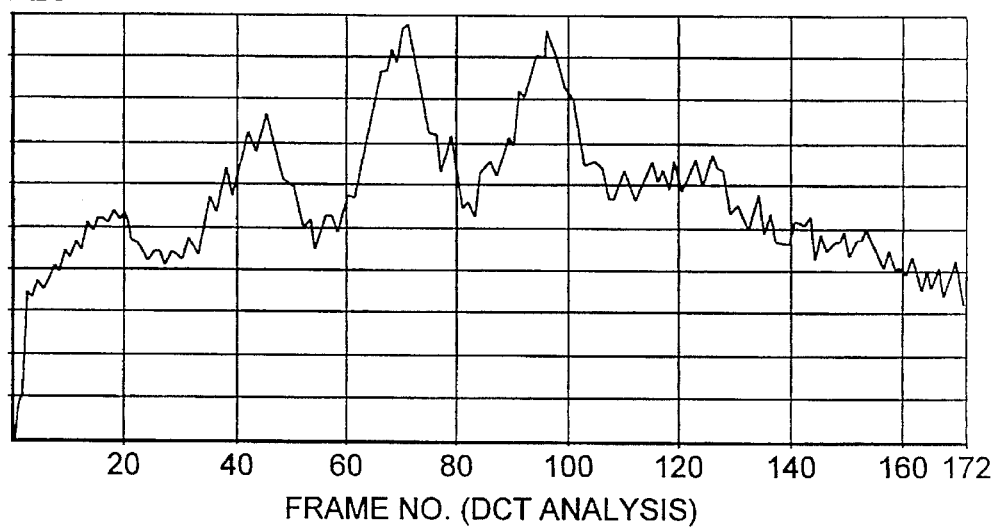

FIG. 7 schematically illustrates an image showing the left coronary arteries at end diastole;

FIG. 8 schematically illustrates an image showing the ! eft coronary arteries (of FIG. 7) at end systole;

FIG. 9 is a graph of the spatial changes (i.e., number of edges)in an angiography sequence for each frame (by number), determined using the spatial analysis technique to process the entire image area in each frame;

FIG. 10 is a graph showing the spatial changes in an angiography sequence for a quarter-size window area of the image in each frame, determined using the spatial analysis technique; and FIG. 11 is a graph showing the sum of amplitudes for the quarter-size window area of the image in each frame, determined using the DCT technique to process compressed digital data representing images produced during the angiography sequence of FIG. 10.

DESCRIPTION OF THE PREFERRED EMBODIMENT

Figure 1:
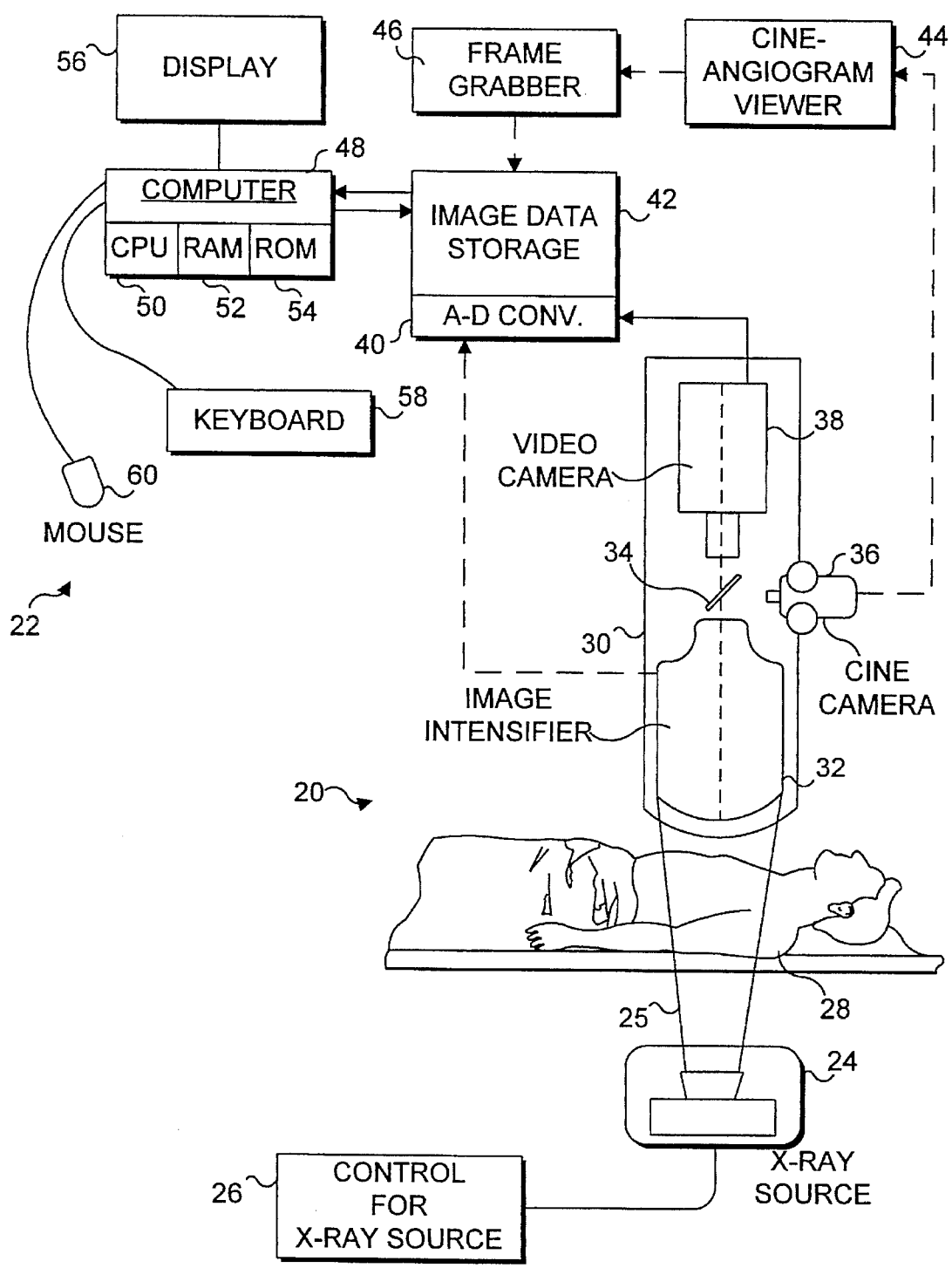
FIG. 1 is a block diagram illustrating an angiography imaging system and components of the present invention that are used to identify specific images, which depict coronary arteries at end systole and end diastole.

With reference to FIG. 1, an exemplary angiography imaging system 20 is illustrated that is suitable for producing angiograms. The angiograms are digitized for use in connection with an analysis system 22 that embodies the present invention. Angiography imaging system 20 includes an x-ray source 24, which produces an x-ray beam 25 when actuated by a control 26. X-ray beam 25 passes through the chest of a patient 28, and more specifically, is generally centered on the heart of the patient. Not shown in FIG. 1 is apparatus used for injecting a radio-opaque contrast substance, such as an iodine compound, through a catheter that is intravascularly inserted into the patient and positioned so that a distal end of the catheter is disposed adjacent an opening into one of the coronary arteries of the heart. For each angiography sequence, a measured quantity of the radio-opaque contrast substance is injected into a selected coronary artery through the catheter. Within the coronary artery, the radio-opaque contrast substance partially absorbs or blocks x-rays, creating a contrast in x-ray images relative to soft tissue and causing the coronary artery to appear as bright lines against a relatively dark background.

An x-ray detector 30 is disposed opposite x-ray source 24, positioned to intercept x-ray beam 25 after it has passed through the chest of patient 28. The x-ray detector includes an image intensifier 32, which converts the x-ray beam into a corresponding optical image. A partially silvered mirror 34 is disposed along the longitudinal axis of x-ray detector 30, so that a portion of the light comprising the image produced by image intensifier 32 is reflected in a direction transverse to the longitudinal axis of the x-ray detector and into the lens of a cine camera 36. The cine camera records on film a series of visually perceptible images in which the coronary arteries are clearly defined. The brightness of the coronary artery increases as the radio-opaque contrast substance diffuses through the arteries, remains stable for a brief period of time, and then decreases as the substance diffuses out of the coronary artery.

Light conveying the image produced by the image intensifier also passes through partially silvered mirror 34 and into a video camera 38. The video camera scans the light conveying the image from image intensifier 32, producing a corresponding analog signal. Alternatively, the light conveying images produced by image intensifier 32 can be projected into an external video camera (not shown). The analog signal produced by the video camera (internal or external to the detector) comprises a voltage, the value of which is indicative of a gray scale value or intensity level for each picture element or pixel in the image. Coupled to video camera 38 to receive the analog signal is an analog-to-digital converter (ADC)40, which converts the voltage representing the gray scale value for each pixel to a corresponding digital value. However, the analog-to-digital conversion may take place directly within the image intensifier, as indicated by the dash line in the figure that couples image intensifier 32 to ADC converter 40.

Alternatively, the film strip of visually perceptible images produced by cine camera 36 can be run through a cine-angiogram viewer 44 of the type commonly used for viewing angiogram film sequences. In connection with the present invention, a frame grabber 46 converts the visually perceptible image recorded on the film strip into corresponding digital data in which each pixel of the image is represented by a voltage having a level that indicates the gray scale value or intensity of the pixel. Frame grabber 46 thus represents an alternative device for digitizing angiogram images recorded on cine camera film strips.

In either case, the digital data corresponding to the gray scale values in the images of the angiography sequence are input to and stored in an image data storage device 42. Typically, image data storage device 42 comprises a large capacity hard drive (greater than one gigabyte) or other suitable non-volatile storage medium. To minimize the storage required for storing the digital data representing each angiogram sequence, the digital image data can be compressed in accordance with the JPEG, MPEG, H.261, or other suitable image compression standard. However, the extent of image compression employed must be limited to minimize unacceptable loss in detail that might impact the accuracy of further analysis and medical diagnostic procedures to be performed on selected frames of the digital imaging data.

Angiography analysis system 22 includes a computer 48 that is coupled to image data storage device 42, enabling the computer to access the image data for each of the angiogram sequences stored therein. Computer 48 is generally conventional in design, comprising a central processing unit (CPU)50, a random access memory (RAM) 52, and a read only memory (ROM) 54, along with other integrated circuitry (not separately shown) that is typically included within an operating computer. Also connected to computer 48 are a display 56, a keyboard 58 and a mouse (or other pointing device-optional) 60. Keyboard 58 and mouse 60 enable the user to input data and/or instructions used for controlling the software running on CPU 50.

In addition to the digital image data stored within image data storage device 42, a program comprising machine instructions executable on CPU 50 is also stored therein. This program enables computer 48 to automatically select specific frames within the digital image data for each angiogram sequence being processed. The specific frames that are selected by the program show the coronary arteries at end systole and at end diastole during each angiography sequence. The images selected at end systole and end diastole in an angiography sequence can be reviewed on display 56 by convening the digital image data for the selected images to a suitable corresponding video signal. In order to process the digital image data for an angiography sequence, an operator instructs computer 48 to run the program stored within image data storage device 42. In response, the machine instructions comprising the program are loaded into RAM 52. CPU 50 then executes the machine instructions.

In connection with the present invention, the program implements a method described below for selecting the specific images depicting a coronary artery at (or near) end systole and end diastole in each angiogram sequence, so that further processing can be carried out to identify or diagnose medical problems in the coronary artery. More particularly, the software selects a preferred end systole and end diastole image from each angiogram sequence. It should also be noted that the software can be used to select images occurring either before or after end systole and end diastole and that the term "specific image" as used in this specification and in the claims that follow is intended to encompass any image referenced by predefined criteria relating to portions of the cardiac cycle. Since typically five or more angiogram sequences are made for a patient at different viewing angles relative to the heart, a medical practitioner using computer 48 can then choose the preferred images showing the coronary arteries at end diastole (and/or end systole) from one or more of the angiogram sequences for further processing and analysis, thereby saving substantial time compared to the conventional approach used to manually identify such images. As noted above, the preferred images of the coronary arteries at end diastole will depict the arteries when filled with a maximum volume of the radio-opaque contrast substance.

Exemplary Images at End Diastole and End Systole

FIGS. 7 and 8 show exemplary left coronary arteries (in a schematic form) at a preferred end diastole and end systole, respectively. No attempt is made in these Figures to represent the left coronary arteries as they truly appear in angiogram images or to show other physiological structures or variations in the background. A catheter 200 is indicated by the dashed lines in the upper portion of each Figure. The radio-opaque contrast substance is injected into the opening of the left coronary artery from the catheter at a point 202. At a preferred end diastole, the heart ventricles are filled with blood to their maximum volume. At that time, the coronary artery is also fully filled with the radio-opaque contrast substance.

In the images shown in FIGS. 7 and 8, processing to determine the total length of edges in each frame occurs within a quarter window 204, which is generally centered within the image, so that the window covers most of the lea coronary artery structure. Specifically, a left anterior descending coronary artery 206 extends through the upper right corner of quarter window 204, and a circumflex coronary artery 208 extends through the let c portion of the quarter window. When the heart muscle is relaxed at end diastole, the total length of the edges of the coronary arteries disposed within quarter window 204 is substantially less than at end systole, when the heart muscle is fully contracted. During the contraction of the muscle, the volume of the heart approaches its minimum and at that instant, more of the left coronary arteries are within quarter window 204 than at end diastole. Thus, by measuring the length of edges within the quarter window in successive frames throughout the angiography sequence, it is possible to identify the end systole frames as those having the local maximum total edge length, while the end diastole frames are those having the local minimum total edge length. A stenosis 210 is evident at end diastole in FIG. 7. The stenosis appears as a restriction in the left anterior descending coronary artery that limits its cross-sectional size at that point.

Steps Implemented to Select Specific Images from an Angiogram Sequence

Figure 2:
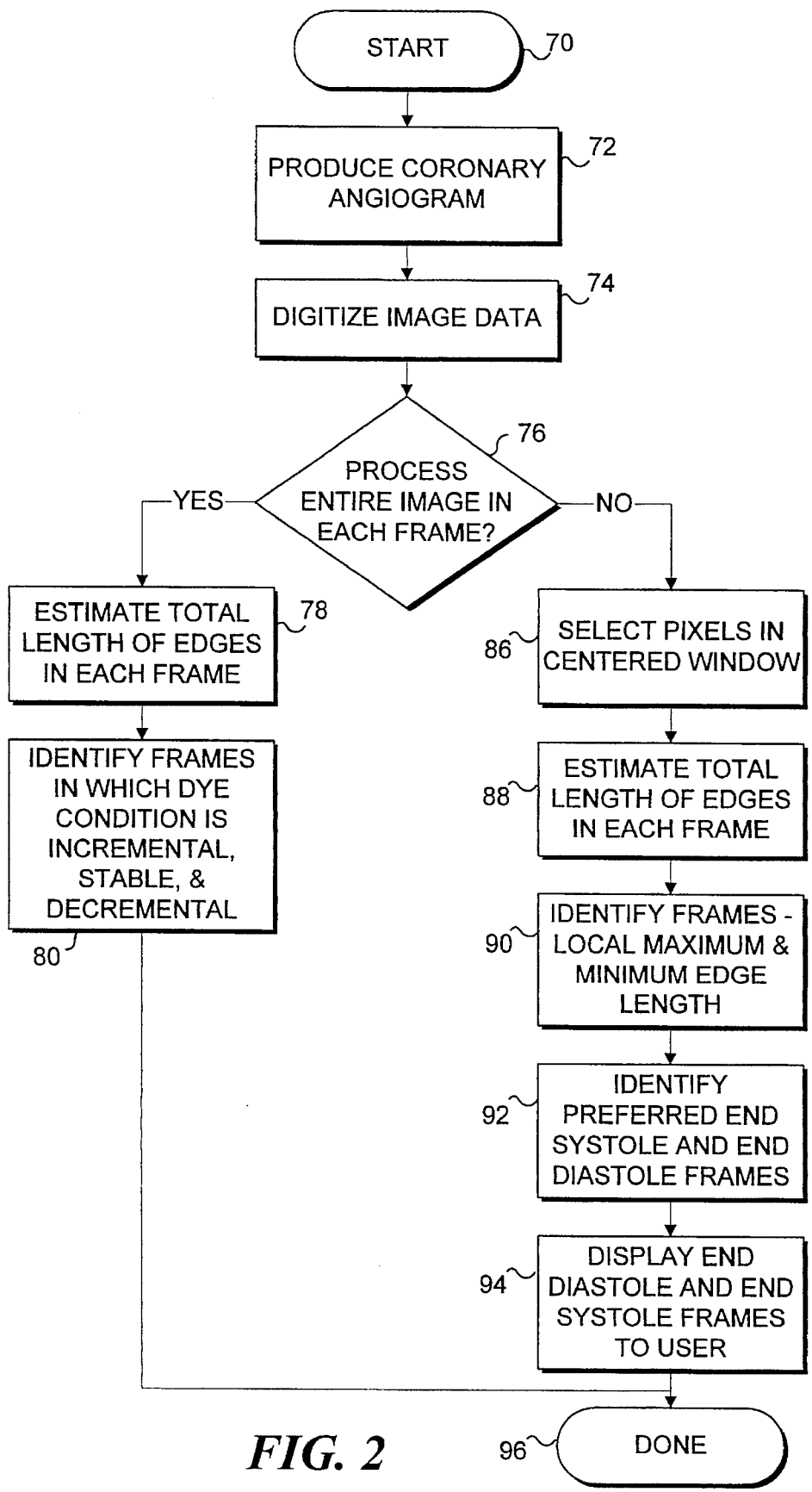
FIG. 2 is a flow chart showing the steps implemented by the present invention.

In FIG. 2, a flow chart illustrates the steps generally implemented by the present invention in automatically selecting specific frames from an angiogram sequence. Beginning at a start block 70, the logic proceeds to a block 72, which calls for producing a coronary angiogram using the apparatus shown in FIG. 1. In a block 74, the images produced during the angiography procedure are digitized, producing corresponding digital image data in which the gray scale values of the pixels in each image are represented by a corresponding digital value.

A decision block 76 determines whether the entire image in each frame should be processed. As will be explained below, processing only a portion of each image yields much greater resolution and allows selecting the frames in which the image depicts the coronary arteries at end systole and end diastole. In the preferred embodiment, a window is employed limiting the portion of the image processed to only one-fourth of the entire image. However, the present invention can also be applied to process the entire image in each frame, to identify three distinct portions of the angiography sequence, which are described below.

If the entire image is to be processed, the logic proceeds to a block 78 in which the total length of edges in each frame is estimated. The term "edges" in block 78 refers to spatial transitions in an image, i.e., a substantial change in the gray scale value. Such spatial transitions occur, for example, at the edge of a coronary artery or at the edge of other physiological structures in an image. An artery appears as a bright line against a darker background. Thus, an "edge" occurs in an image where the gray scale values of adjacent pixels are substantially different. In addition to spatial transitions that occur at the edges of coronary arteries, the pixels in the images may also change between bright and dark at the edge of the patient's diaphragm, spine, or at the edges of other physiological portions of the body in the images that have a substantially greater opacity to x-rays than the surrounding soft tissue.

For a given angiography sequence, the edges of physiological components of the body such as the spine remain relatively constant. However, the edges of the coronary arteries become gradually more apparent or brighter as the radio-opaque contrast substance diffuses into the coronary arteries. This portion of the angiography sequence in which the radio-opaque contrast substance fills the arteries is sometimes referred to as the "incremental" portion. It is followed by the "stable" portion, in which the contrast between the coronary arteries and the background remains relatively constant, and then by the "decremental" portion of the sequence in which the brightness in the arteries gradually fades as the radio-opaque contrast substance diffuses out of the coronary arteries. The graph shown in FIG. 9 illustrates these three portions of the angiography sequence.

The present technique can readily identify the three different portions of an angiography sequence based upon the change in the total length of the edges within the portion of the image being processed. The identification of the three portions is relatively simple, since the number of edges in successive frames generally increases during the incremental portion, remain relatively high during the stable portion, and then, generally decrease during the decremental portion of the angiography sequence.

This process may be useful to identify the image frames in which a structure of the heart is maximally opacified by the radio-opaque contrast substance. However, for the purpose of automatically selecting the image frames of a coronary angiogram for diagnostic analysis, it is also necessary to identify, in addition, the frames that lie at (or near) end diastole and end systole.

The preferred application of the present method follows a logic path to the right of decision block 76, which calls for processing only a portion of the image in each frame. Specifically, in the preferred embodiment, the portion of each frame that is processed comprises a centered window encompassing approximately one-fourth of the entire image area. In a block 86, the digital data corresponding to pixels disposed in the centered window are selected for processing. Using only the digital data corresponding to these selected pixels, a block 88 provides for estimating the total length of the edges in each frame.

During a complete angiography sequence, the patient's heart will normally experience a number of cardiac cycles, each of which includes an end diastole and an end systole. Accordingly, in a block 90, the program estimates a local maximum and local minimum edge length within the frames of the sequence. The edge length increases to a local maximum in the frame in which the coronary arteries are depicted at end systole and decrease to a local minimum in those frames in which the coronary arteries are depicted at end diastole. From the series of end systole and end diastole frames identified in an angiography sequence, a preferred end systole frame is selected that has the greatest maximum edge length of all of the frames in the sequence. The end diastole frame that immediately precedes this end systole frame in the angiography sequence is selected as a preferred end diastole frame. If two consecutive end systole frames have an equal value for maximum edge length, then the preferred end diastole frame the end diastole frame (i.e., the Frame with the minimum edge length) occurring between those two end systole frames. In a block 92, the preferred end systole and end diastole frames in the angiography sequence are thus identified. Thereafter, at the operator's discretion, the end diastole and end systole frames can be displayed for further processing as noted in a block 94, or for selection of optimum preferred frames from among each of the plurality of angiography sequences typically performed on the patient. The preferred frames for each sequence are identified by an angiography sequence number and a frame number, enabling the preferred frames to be indexed and stored in image data storage device 42 (or other non-volatile memory - not shown) as part of a patient medical history. The procedure terminates at a block 96.

Figure 3:
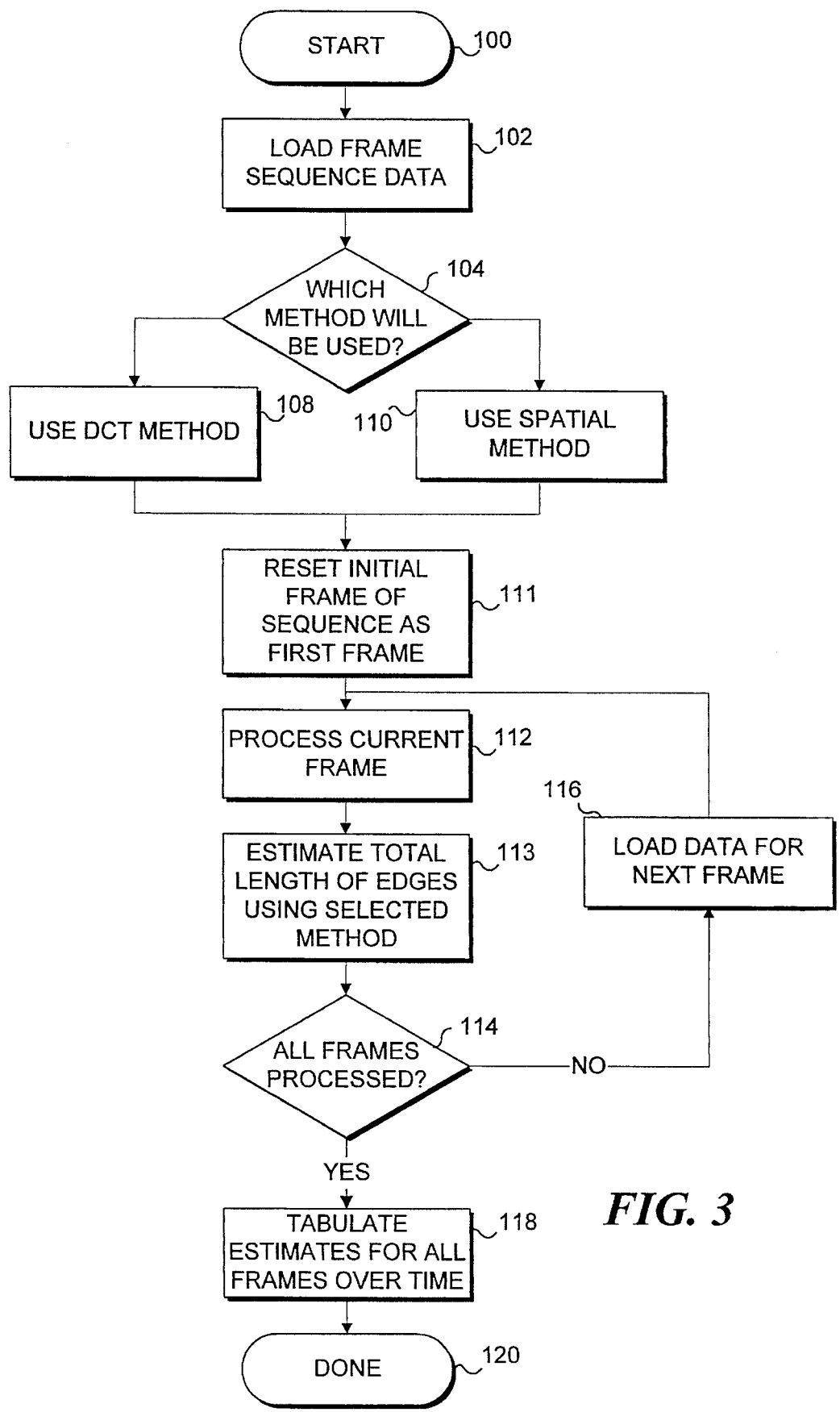
FIG. 3 is a flow chart showing the steps used to estimate the total length of edges in each frame of the angiography sequence.

Further details of the steps involved in estimating the total length of the edges in each frame are shown in FIG. 3. Following a start block 100, a block 102 provides for loading the digital image data corresponding to one of the angiography sequences performed on the patient. The digital image data loaded in this step, as noted above, represent the gray scale values of pixels in the images of the sequence. If the digital image data have been compressed, the gray scale values are represented as DCT components.

A decision block 104 determines whether a spatial method or a DCT method is to be used to process the digital data for the current frame. The DCT method is normally used only for processing compressed digital data. If the digital image data are not in a compressed format, the total length of the edges in the current frame are estimated using the spatial method, as noted in a block 110. Conversely, if the digital image data are compressed, a block 108 provides for estimating the total length of the edges in the current frame using the DCT method. The steps of each of these methods are described in further detail below.

In a block 111, the process is reset to an initial frame of the sequence, which represents the first frame to be analyzed. In a block 112, the first frame (now the current frame) is processed, using the method selected in decision block 104. The selected method returns an estimate of the total length of edges, as noted in a block 113. If the DCT is used for this determination, the estimate is based on a measure of the amplitudes of low frequency components.

A decision block 114 determines if all frames in the current angiography sequence have been processed. If not, the logic proceeds to a block 116, which loads the digital image data for the next frame in the sequence. The logic then returns to block 112, to repeat the processing of the data for the frame that was just loaded.

After all frames in the sequence are processed, the estimates for all of the frames are tabulated over the time of the angiography sequence, as noted in a block 118. This step provides for indexing the end systole and end diastole frames identified during the sequence so that further steps shown in the flow chart of FIG. 2 can be implemented. Once the estimates have been tabulated, this routine is completed, as noted in a block 120.

Figure 4:
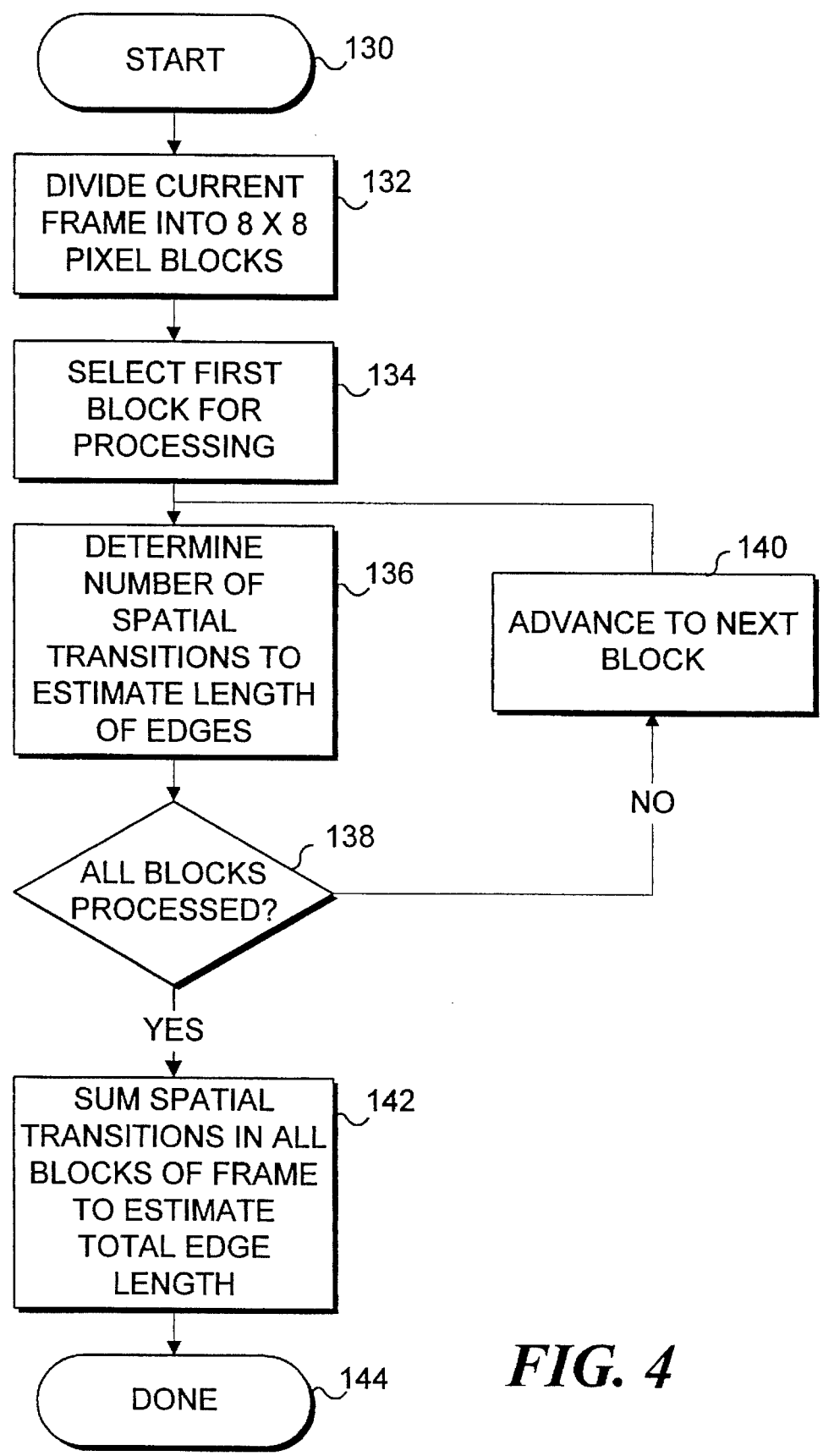
FIG. 4 is a flow chart illustrating the details of the spatial analysis technique used in the present invention.

Details of the step carried out in block 110 of FIG. 3 are illustrated in the flow chart shown in FIG. 4, beginning at a start block 130. In a block 132, the portion of the current frame being processed is divided into blocks that are 8×8 pixels in size. Since the image digital data are being processed rather than the actual image, this steps corresponds to creating a series of arrays of the digital image data representing the pixels in the blocks, wherein each array includes the digital image data for a different block of pixels. Although the preferred embodiment uses blocks that are 8×8 pixels, it should be apparent that this size was selected for convenience for processing frames that are 512×512 pixels in size. For other angiography imaging system, the frames may be different sizes, e.g., 1024×1024 pixels, 900×900 pixels, or even 256×256 pixels. Although frames significantly smaller than 512×512 pixels are unlikely to be used because they present inadequate information, the present invention is still applicable.

The selection of a block that is 8×8 pixels in size in the preferred embodiment is a compromise between speed and accuracy. Traditional edge detection techniques are typically applied to single pixels, whereas average gray level methods typically process the entire image as a single block. For the present invention, it will be apparent that the larger the block size, the less accurate will be the result; similarly, the smaller the block size, the greater will be the amount of computation required. However, minor changes in block size, e.g., 10×10 pixels or 5×5 pixels, will not significantly impact either the speed or accuracy of the present invention.

In a block 134, the first pixel block is selected for processing. A block 136 in the flow chart next provides for determining the number of spatial transitions in the current pixel block being processed. A spatial transition occurs in the pixel block when there is a significant change in the gray scale values associated with the pixels in the rows or columns of data comprising the array. Thus, the step in block 136 enables the program to estimate the total length of edges in the pixel block being processed.

Figure 5:
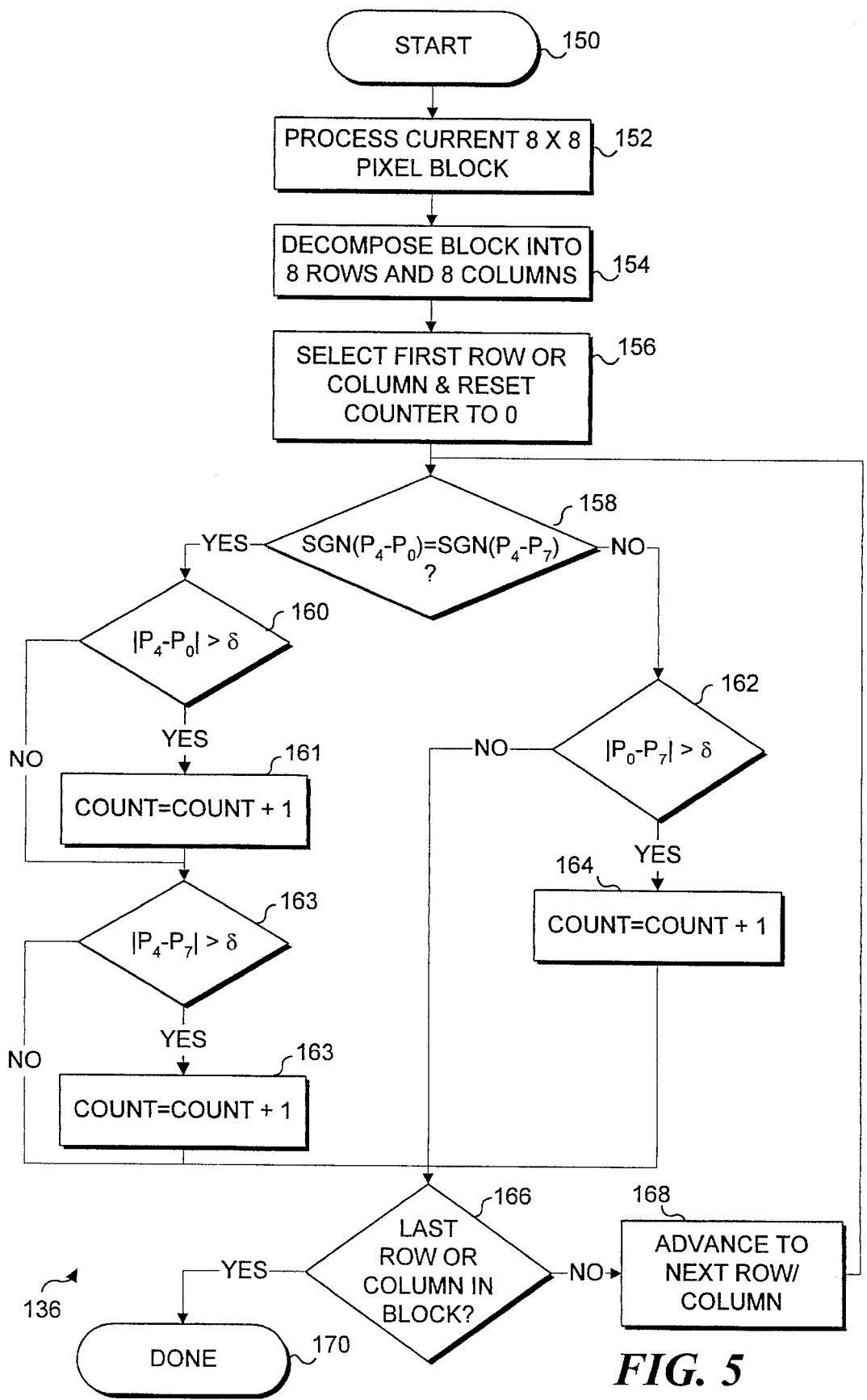
FIG. 5 is a flow chart illustrating further details of the steps used to count edges in a block of pixels in each frame, in the spatial method.

At this point, it is helpful to consider further details of the step identified in block 136 of the flow chart, which are shown in FIG. 5. Beginning at a start block 150, the logic proceeds to a block 152, which indicates that the current 8×8 pixel block is being processed. Processing of the current pixel block is effected as noted in a block 154 by decomposing it into eight rows of pixels and eight columns of pixels so that the digital image data for the pixels comprising each row and column can be analyzed to determine where edges or spatial transitions occur. The eight rows are successively processed, followed by the eight columns.

In a block 156 of the flow chart, the first row or column in the current 8×8 pixel block is selected and an edge transition counter is reset to zero. A decision block 158 determines if a two-edge model applies. The current preferred embodiment assumes that in an eight pixel row or eight pixel column, only a limited number of edges can occur, i.e., eight successive pixels in an image that is 512×512 pixels in size can include up to two edges. However, similar results can be achieved using a different size pixel block with a corresponding different number of edges or gray scale transitions in each row/column. Generally, the more pixels in a row or column, the greater will be the number of transitions or edges that may occur therein.

The number of edges or transitions in a row or column depends upon the values of the differences between the gray scale values of specific pixels within the row or column. The gray scale values of the pixels in a row or column of eight pixels can be represented by the variable $P_i$, where i=0, 7. In the preferred embodiment, the specific pixels (gray scale values) that are processed in each row and column are $P_0$, $P_4$, and $P_7$, i.e., the first, fifth, and eighth pixels; however, it is clear that the gray scale values of other pixels could be used. In regard to these three pixels within the current row or column being processed, the program evaluates the following conditions:

$$sgn(P_4-P_0)=sg(P_4-P_7) \quad (1)$$

$$|P_4-P_0|>\delta \quad (2)$$

$$|P_4-P_7|>\delta \quad (3)$$

$$|P_0-P_7|>\delta \quad (4)$$

where "sgn" is the sign (+ or −) of the indicated difference, and δ is a threshold value (a predefined constant in the present embodiment). If the condition defined in Equation (1) is met in a decision block 158, a decision block 160 in the flow chart determines if the condition in Equation (2) is met, and if so, a block 161 increments the edge count by one. If the result in decision block 158 is negative, a decision block 162 determines if the condition in Equation (4) is true, and if so, a block 164 increments the value of the edge count by one. If not, the logic proceeds to a decision block 166.

If the response to decision block 160 is negative and following block 161, the logic determines if the condition of Equation (35) is true, and if so, a block 163 increments the value of the edge count by one. Thereafter, or if the condition in decision block 163 is not met, the logic continues with decision block 166. Decision block 166 determines if the last row or column in the current block has been processed. If not, a block 168 advances to the next row/column and returns to decision block 158 to process that row or column.

Once all rows and columns in the current pixel block have been processed, yielding a total edge count, Tj for the jth pixel block, the logic proceeds to a block 170, which terminates processing for the current pixel block. The logic then returns to the flow chart in FIG. 4, at a decision block 138. Decision block 138 determines if processing of all pixel blocks in the portion of the current image being processed is complete, and if not, proceeds to a block 140, which advances to the next pixel block. Subsequently, the logic returns to block 136, iterating the steps in FIG. 5 for the rows and columns of the next pixel block. If all of the pixel blocks have been processed, the next step is implemented in a block 142.

In block 142, the number of spatial transitions, i.e., the value returned by the variable "count" for each of the blocks in the portion of the frame being processed are summed in order to estimate a total edge length, $T_{frame}$, for the frame:

$$T_{frame}=\sum_{j=1}^{N} T_j \quad (5)$$

where N is the number of blocks in the portion of the frame being processed. Thereafter, this routine terminates in a block 144.

Figure 6:
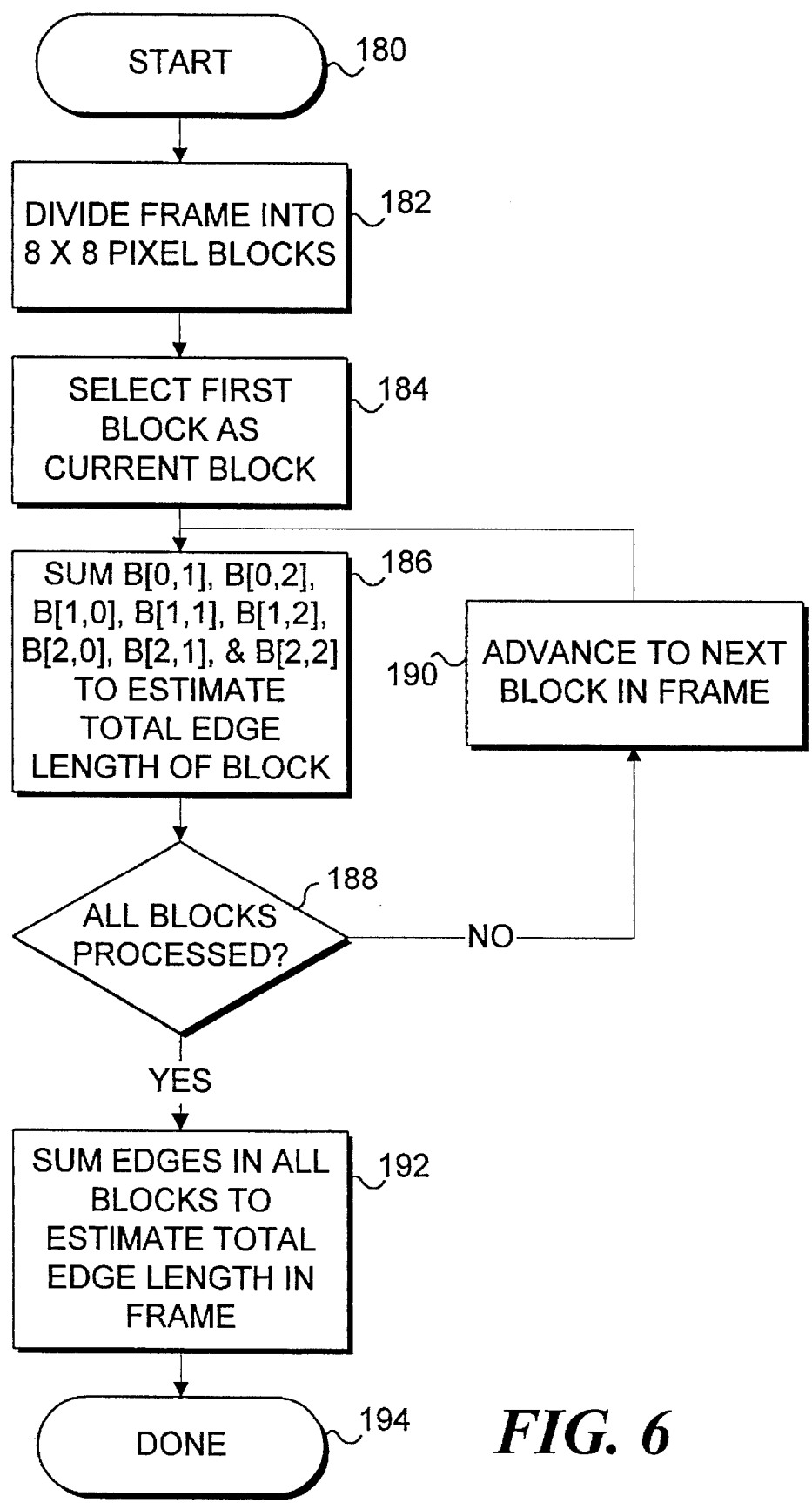
FIG. 6 is a flow chart illustrating the details of the DCT technique used in another embodiment of the present invention to estimate the total length of the edges in each frame.

If the DCT method noted in FIG. 3 is used instead of the spatial method, the program processes compressed digital image data, as shown in FIG. 6, beginning at a start block 180. In a block 182, the digital image data for the portion of the frame being processed is divided into components representing 8×8 pixel blocks, just as in the spatial method for processing the data; however, the gray scale values for each pixel in the block are not simply represented as a digital value. Instead, the compressed digital image data represent the gray scale values of the pixels in the block in terms of their corresponding DCT components, i.e., the components resulting from performing a DCT on the gray scale values for the pixels in the block. In a block 184 of the flow chart, the compressed digital image data representing the first 8×8 pixel block are selected for processing. Next, in a block 186, the DCT components for the current pixel block are processed. Most of the image energy in the discrete cosine domain is concentrated in the low frequency components, and only the low frequency components that are used in this method. These DCT components are identified by the variable B[i,j], where i=0, 2 and j=0, 2. The component B[0,0] corresponds to the average gray scale value over all pixels in the block and is therefore ignored. Components greater than B(2,2) can also ignored in this application.

Exclusion of the higher frequency components is not mandatory to the process. These components can be used in addition to the low frequency components. However, the result obtained by including higher frequency components will be similar to the result obtained using only low frequency components, because the high frequency components represent noise in the image and contribute only a small amplitude.

The total edge length $T_k$ of the $k_{th}$ pixel block is defined by:

$$T_k=\Sigma B[0,1]+B[0,2]+B[1,0]+B[1,1]+B[1,2]+B[2,0]+B[2,1]+B[2,2] \quad (6)$$

A mathematical development explaining the use of the DCT components in determining the total edge length for each pixel block follows below.

In a decision block 188, the program determines if all of the pixel blocks have been processed, and if not, proceeds to a block 190. In block 190, the logic advances to the next pixel block in the portion of the frame that is being processed.

After processing of all pixel blocks in the portion of the image involved is complete, a block 192 provides for summing the length of the edges of all of the blocks previously processed to estimate the total edge length for the frame. Once this step is completed, this routine terminates in a block 194.

As mentioned in the description of the spatial method, image size may not necessarily be 512×512 pixels. In the event the a lower resolution image is analyzed using the present invention, it may be advisable to include medium frequency components (e.g., components 3 to 5) in addition to the lower frequency components used in the preferred embodiment.

Comparative Graphs

In FIG. 9, the spatial analysis method is applied to the entire image in each of 172 frames comprising a representative angiography sequence. The incremental, stable, and decremental portions of the sequence are clearly evident in FIG. 9, based upon trends in the total length of the edges that occur in the frames during the sequence. Also evident in the graph are systolic and diastolic portions of the cardiac cycle, wherein the successive local maximum in the number of spatial transitions per frame, particularly evident in the stable portion of the angiography sequence, indicate the end systole portion of each cardiac cycle; the local minimums conversely indicate the frames in which the end diastole portion of the cardiac cycle has occurred.

In FIG. 10, the spatial analysis method is applied to a centered one-quarter image area window. A preferred frame for end systole and a preferred frame for end diastole are clearly apparent in the graph. The preferred end systole frame is the frame in which a maximum number of spatial transitions or edges are identified. Similarly, the end diastole frame is the frame having a minimum number of edges that immediately precedes the preferred end systole frame. In addition, other frames having a local maximum and a local minimum number of spatial transitions or edges at end systole and end diastole in other cardiac cycles are apparent in the graph.

In FIG. 11, the DCT analysis has been applied to the same angiography sequence as in FIG. 10, yielding almost identical results. Thus, it will be apparent that if compressed image data are available, a preferred end systole and a preferred end diastole frame can be identified with substantially the same accuracy using either the DCT method or the spatial method.

Comparisons of the frames identified as corresponding to end systole and end diastole by either of the two methods used in the present invention have been found to correspond almost identically to the frames selected manually by a skilled medical practitioner, thereby confirming the utility of the present invention. This invention can automatically select specific flames and present them to a physician in each of a plurality of angiography sequences, enabling the physician to quickly choose, from among the automatically selected frames in each of the sequences, those frames that are to be used for further analysis. Considerable time savings can result from this automated technique. Further, by storing only the digital image data for frames selected by the technique, substantially less storage space is required to maintain a patient history. Since the selected frames are already indexed, it is relatively easy to reference the specific frames selected by the technique from amongst the original images.

Although the preferred embodiment has used a quarter window that is generally centered within the image, it will be apparent that the portion of the entire image that is processed can be automatically determined. For example, by repeating the method on the digital image data for blocks of pixels within windows disposed at different locations within the image, it should be possible to select a best position for the window in which the differences between the total length of edges at end systole and end diastole is a maximum. Generally, the best position should be approximately centered over the coronary artery structure. Further optimization in the size of the window used can also be achieved in the same manner, by selecting a size for the window that yields a maximum difference in the total length of the edges at end diastole and end systole.

Application of the spatial method for determining the total length of edges in the portion of the frame being analyzed uses a threshold. Currently, the threshold is determined empirically ($\delta=20$). Instead, it would be preferable to automatically determine a threshold, using the following method. From a sequence of digital images in uncompressed format, three image frames that lie approximately in the middle of the sequence are randomly selected. Each of the images is divided in its entirety into blocks of 8×8 pixels (or other appropriate size blocks). In every 8 pixel row and every 8 pixel column of each pixel block, the absolute difference in gray scale value between specific pixels positions, e.g., the first, fifth, and eighth positions, are determined, yielding values such as: $|P_4-P_0|$, $|P_4-P_7|$, and $|P_0-P_7|$. These three differences are determined for every row and column in each block of the image. A histogram h(t) of the frequency distribution of all difference values, t, is prepared for each image. For images with an eight-bit gray scale, the range of the difference t will lie in the range 0 through 255. A cumulative function, P(t), is then prepared from the histogram:

$$P(t) = \sum_{n=t}^{255} h(n) \tag{7}$$

This cumulative function shows the accumulated sum of the frequency of each difference value. The threshold is determined from the cumulative function as the value of t having a cumulative frequency distribution, f. It is anticipated that a reasonable value for f will lie in the range from 5% to 25%. The actual value for f will be determined empirically.

Due to the variation of the gray scale values and the effect of end diastole and end systole, the cumulative difference function is calculated for all three frames, and the threshold is determined from the average of the curves from the three frames. It is noted that a minimum number of three frames should be used to automatically determine the threshold.

Various medical procedures require tracking of the end systole and end diastole portions of the cardiac cycle. Accordingly, the present method may have application to such procedures for use in determining when these portions of the cardiac cycle occur. Since the processing required to identify the time of end systole and end diastole can be done in real time, the present invention can be used to monitor these conditions for input to other procedures.

Mathematical Development of the DCT Analysis Method

The Fourier transform is often used for analyzing time varying periodic processes in the frequency domain, by decomposing the periodic data into a sum of sinusoidal functions. Data that occurs over a finite time can be decomposed into N complex sinusoidal components, as shown in the following equation:

$$H(u) = \frac{1}{\sqrt{N}} \sum_{j=0}^{N-1} h(j) \exp\left\{\frac{-2\pi uij}{N}\right\} \tag{8}$$

where h(j) are the complex sinusoidal components. To covert H(u) back to h(j), the following inverse discrete Fourier transform (DFT0 is performed:

$$h(j) = \frac{1}{\sqrt{N}} \sum_{u=0}^{N-1} H(u) \exp\left\{ \frac{2\pi u i j}{N} \right\} \quad (9)$$

The DFT can be extended to two or higher dimensions. A discrete N×N two-dimensional signal h(j,k) and its corresponding N×N two-dimensional signal H(u,v) in the DFT domain have the following relationships:

$$H(u,v) = \frac{1}{N} \sum_{j=0}^{N-1} \sum_{k=0}^{N-1} h(j,k) \exp\left\{ \frac{-2\pi i(uj+vk)}{N} \right\} \quad (10)$$

$$h(j,k) = \frac{1}{N} \sum_{u=0}^{N-1} \sum_{v=0}^{N-1} H(u,v) \exp\left\{ \frac{2\pi i(uj+vk)}{N} \right\} \quad (11)$$

Each frequency component in the DFT domain represents an amplitude of a sinusoidal wave at a specific frequency. When a 16×16 block of pixels in an angiography image is processed using the DFT, the gray scale data are decomposed into a new block that includes a constant (DC) value and values for the periodically varying (AC) frequency components. The constant or DC value is the average gray scale level intensity for the block. The AC amplitude values provide more detailed information about the gray scale value distribution in the block of the image. In the present application, only the AC components corresponding to up to two edges need be used. For example, frequency components (1,0) and (0,1) represent the single edge model in the x and y directions (row and column) for the block. Similarly, the frequency component (2, 1) represents a two-edge model in the x direction and a one-edge model in the y direction. The exact total edge length in the block can be estimated by summing all of the frequency components for the block. However, because the higher frequency components are not of any interest in this application, it is only necessary to sum the components in which x or y are equal to 1 or 2. For low resolution images, for example 256×256 pixels, it may be advisable to use higher frequency components, such as 3 through 5. Since the intensity value of a normal edge in an angiogram image changes relatively gradually over the image space, summing only the low frequency components yields an acceptable value for the total edge length $T_B$, which is a measure of the volume of injected radio-opaque contrast substance in the portions of the coronary arteries disposed within the block:

$$T_B = \sum_{u=0}^{2} \sum_{v=0}^{2} H(u,v) - H(0,0) \quad (12)$$

where H(u,v) is the spectral component in the DFT domain. It will be evident that the DCT can be applied to the gray scale values comprising the digital image data (uncompressed) to determine the edge length in each of the pixel blocks in each frame. The edge lengths for all of the pixel blocks in the frame are summed to determine a total edge length for the frame. Based upon the total edge length for the frames in an angiography sequence, the preferred end diastole and end systole frames can be selected as described above. The DFT technique is thus a further alternative to the spatial method for determining the total edge length in the frames using uncompressed digital image data.

A Fourier series of any continuous real and symmetric function contains only real coefficients corresponding to the cosine terms. For an N×N signal h(j,k), a symmetric 2N×2N array $h_s(j,k)$ can be obtained by mirroring the signal to the -x and -y axes. Applying Equation (9) to such a signal yields:

$$H_s(u,v) = \quad (13)$$

$$\frac{1}{2N} \sum_{j=-N}^{N-1} \sum_{k=-N}^{N-1} h_s(j,k) \exp\left\{ \frac{-2\pi i}{2N} \left[ u\left(j+\frac{1}{2}\right) + v\left(k+\frac{1}{2}\right) \right] \right\}$$

for u,v=–N, ..., –1,0,1, ..., N. Because h(j,k) is real and symmetric about the axes, Equation (13) reduces to:

$$H_s(u,v) = \frac{2}{N} \sum_{j=0}^{N-1} \sum_{k=0}^{N-1} h_s(j, \quad (14)$$

$$k) \cos\left[ \frac{\pi}{N} u\left(j+\frac{1}{2}\right) \right] \cos\left[ \frac{\pi}{N} v\left(k+\frac{1}{2}\right) \right]$$

Equation (14) is actually the DCT of h(j,k). From this relationship, it should be apparent that the spectrum in the DCT domain over an N×N block is similar to the spectrum in the DFT domain over a 2N×2N block. When applying the DFT, a 16×16 pixel block was used. The DCT is applied to 8×8 pixel blocks to achieve a comparable result. The DCT of an 8×8 pixel block is as follows:

$$H(u,v) = \frac{1}{4} C(u)C(v) \sum_{j=0}^{7} \sum_{k=0}^{7} h(j, \quad (15)$$

$$k) \cos\left[ \frac{\pi}{8} u\left(j+\frac{1}{2}\right) \right] \cos\left[ \frac{\pi}{8} \left(k+\frac{1}{2}\right) \right]$$

where u,v=0 ..., 7, and $$C(u) = \begin{cases} \frac{1}{\sqrt{2}} & u=0 \\ 1 & \text{otherwise.} \end{cases}$$

To determine the total edge length for the block using the DCT method, value of H(u,v) from Equation (15) is substituted into Equation (12). However, since the compressed form of the digitized image data are created by applying a DCT to the digitized image data, the DCT components used to determine the total edge length for each block have already been determined and can readily be extracted from the compressed digital image data. It is not necessary to determine the inverse DCT. Use of the compressed data thus greatly simplifies the determination of total edge length in the frames of the sequence when the DCT method is used.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for automatically selecting specific images from a plurality of images produced during a coronary angiography procedure, said specific images that are selected depicting a defined portion of a cardiac cycle, said method comprising the steps of:

(a) providing digital data representing each of the plurality of images, said digital data including digital values for each of a plurality of picture elements comprising each image;

(b) using the digital data for each image, determining a total length of edges in at least a portion of each image, by detecting differences in the digital data for picture elements disposed on opposite sides of an edge; and (c) as a function of the total length of the edges in each image, selecting the specific images that depict the defined portion of the cardiac cycle from the plurality of images.

2. The method of claim 1, wherein the step of determining the total length of the edges in each image comprises the steps of:

(a) dividing at least a portion of each image into a plurality of contiguous sections, each section comprising a predetermined number of the picture elements arrayed in rows and columns;

(b) identifying and counting the edges disposed in each of the rows and columns of the section based upon the differences in the digital data for the picture elements within each row and each column of the section, said differences indicating that edges of the coronary arteries pass through the rows and the columns;

(c) summing the edges passing through the rows and columns comprising the section to determine a number of edges within the section;

(d) repeating steps (b) and (c) of this claim for each of the sections comprising each image; and (e) summing the number of edges within the sections of each image, to determine the total length of the edges in the image.

3. The method of claim 2, wherein the defined portion of the cardiac cycle comprises one of an end systole and an end diastole, and wherein the step of selecting the specific images that depict the defined portion of the cardiac cycle comprises the steps of:

(a) identifying a first set of specific images having a local maximum total length of the edges, compared to the total length of the edges in images that precede and follow each of the first set of specific images;

(b) identifying a second set of specific images having a local minimum total length of edges, compared to the total length of the edges in images that immediately precede and follow each of the second set of specific images; and (c) classifying the first set of specific images as end systole images and the second set of specific images as end diastole images.

4. The method of claim 2, wherein the digital data comprises gray values; and wherein the step of identifying and counting comprises the steps of determining differences in gray values for selected picture elements in each row and column and comparing the differences to a threshold value.

5. The method of claim 3, wherein a preferred end systole image comprises one of the end systole images that has a maximum total length of edges, and a preferred end diastole image comprises one of the end diastole images immediately preceding or following the preferred end systole image.

6. The method of claim 1, wherein the step of determining the total length of the edges in each image comprises the steps of:

(a) dividing at least a portion of each image into a plurality of contiguous sections, each section comprising a predetermined number of picture elements arrayed in rows and columns;

(b) determining a Fourier transform of the digital data for each section;

(c) as a function of Fourier transform, determining a number of edges in the section; and (d) summing the edges for the sections in each image to determine the total length of the edges for the image.

7. The method of claim 1, wherein the digital data for the images are in compressed form, and wherein the compressed form of the digital data comprises discrete cosine transform components.

8. The method of claim 7, wherein the step of determining the total length of the edges in each image comprises the steps of:

(a) dividing at least a portion of each image into a plurality of contiguous sections, each section comprising a predetermined number of picture elements arrayed in rows and columns;

(b) as a function of the discrete cosine transform components comprising the digital data, for each section, determining a number of edges in the section; and (c) summing the number of edges for the sections in each image to estimate the total length of the edges for the image.

9. The method of claim 1, further comprising the step of visually displaying the specific images that depict the defined portion of the cardiac cycle from the plurality of images.

10. The method of claim 1, further comprising the step of storing the digital data for the specific images that depict the defined portion of the cardiac cycle from the plurality of images, indexed so as to identify the specific images from among the plurality of images.

11. The method of claim 1, further comprising the steps of repeating steps (a) through (c) of the claim, for each of a plurality of image sequences produced during the angiography procedure on a patient.

12. The method of claim 4, wherein the threshold value is determined by:

(a) selecting a plurality of mid-sequence images produced generally at a mid-point of the angiography procedure;

(b) determining a histogram of the differences in the gray scale values for the selected picture elements in each section of the mid-sequence images;

(c) determining a cumulative function from the histogram that is a function of an accumulated sum of a frequency of each difference value; and (d) selecting as the threshold a value of the cumulative function that corresponds to an empirically determined frequency.

13. The method of claim 2, wherein the portion of the image that is divided into the sections comprises a relatively small area of each image that is generally disposed at a common position in each of the images, further comprising the step of repeating steps (b) through (e) of claim 2 for a plurality of different positions of the small area in the images, to obtain the total length of the edges in each image for each position of the small area.

14. The method of claim 13, further comprising the step of selecting a preferred position of the small area in the images for use in depicting the defined portions of the cardiac cycles, said preferred position being selected based upon differences in the number of edges in the images depicting an end systole and an end diastole of the cardiac cycle for each position of the small area in said images.

15. The method of claim 14, wherein the preferred position yields a greater difference in the number of edges in the small area of the images depicting the end systole and the end diastole, compared to corresponding differences in the number of edges determined with the small area at other positions in said images.

16. The method of claim 2, wherein the portion of the image that is divided into the sections comprises an area of each image that is generally less than a total area of the image, further comprising the steps of repeating steps (b) through (e) of claim 2 for a plurality of different size areas in the images, to obtain the total length of the edges in each image for size of the area, and selecting a preferred size of the area based upon differences in the total number of edges in the images for each of the different sizes of the area.

17. A method for selecting specific images from a plurality of angiography images, said specific images depicting coronary arteries at an end systole and at an end diastole of the cardiac cycle, comprising the steps of:

(a) providing digital data corresponding to the plurality of angiography images, said digital data indicating gray scale values for a plurality of pixels comprising the images;

(b) dividing at least a portion of each image into blocks of pixels, each block comprising a plurality of rows and columns of pixels;

(c) from the digital data for the rows and columns of pixels in one of the blocks, determining a number of edges disposed within said block, based on changes in the gray scale values that occur across each edge;

(d) for each image, determining a total length of the edges within an area of the image in which the blocks are disposed; and (e) based upon temporal changes in the total length of the edges in each image, selecting images that depict the coronary arteries at the end systole and at the end diastole of the cardiac cycle, an image that depicts the coronary arteries at the end systole having a substantially greater total length than an image that depicts the coronary arteries at the end diastole.

18. The method of claim 17, wherein the digital data are in a compressed form, so that gray scale values in the images are indicated using discrete cosine transform components.

19. The method of claim 18, wherein the steps of determining the number of edges in each block and of selecting the images comprise the step of determining a discrete cosine transform for each of the blocks, using the discrete transform components comprising the digital data.

20. The method of claim 17, wherein the step of determining the number of edges in the block comprises the steps of comparing differences between the gray scale values for selected pixels in each row and in each column of the block, to a threshold and to each other, and as a function of changes in the gray scale values, determining the number of edges in each row and column of the block.

21. The method of claim 20, wherein the threshold is empirically determined so as to ensure that there is a substantial difference in the total length of the edges in the images depicting the coronary arteries at the end systole and the end diastole.

22. The method of claim 17, wherein the portion of the images divided into blocks comprises a window that is substantially smaller in area than each image.

23. The method of claim 22, wherein the window is disposed within the images at a position that encompasses a substantial portion of the coronary arteries.

24. The method of claim 23, further comprising the steps of repeating steps (a) through (e) in claim 16 with the window disposed at each of a plurality of different positions, and selecting a preferred position for the window based upon differences of the total length of the edges when the window is disposed at said plurality of different positions.

25. The method of claim 24, wherein the preferred position is selected by choosing a position for the window by comparing differences in the total length of the edges in images depicting the coronary arteries at the end systole and the end diastole, determined with the window at each of the plurality of different positions of the window, and selecting the position of the window that yields a greatest difference in the total length of the edges in the images, as the preferred position.

26. A system for automatically selecting specific images from a plurality of images produced during a coronary angiography procedure, said specific images that are selected depicting coronary arteries during a defined portion of a cardiac cycle, said system comprising:

(a) a digitizer that converts visual images into digital data, said digital data representing gray scale values for a plurality of picture elements comprising the images produced during the coronary angiography procedure;

(b) a computer coupled to the digitizer to receive the digital data, said computer including:
 (i) a central processing unit that executes machine instructions, said machine instructions comprising a program for processing the digital data to select the specific images;
 (ii) non-volatile storage for the digital data; and
 (iii) a memory used to store the machine instructions for execution by the central processing unit; and (c) said central processing unit while executing the machine instructions comprising:
 (i) means for selecting the digital data corresponding to blocks of the picture elements in each image, for each image said blocks representing the digital data for at least a portion of the image that is disposed at a position common to each image, the picture elements of each block comprising a plurality of rows and columns;
 (ii) means for processing the digital data for each of the blocks to determine a total length of the edges disposed within each image; and
 (iii) means for selecting the specific images depicting the defined portion of the cardiac cycle based on temporal differences in the total length of the edges disposed within each image.

27. The system of claim 26, wherein the digital data are in a compressed form in which the gray scale values of the picture elements are represented by discrete cosine transform components.

28. The system of claim 27, wherein the means for processing determine the total length of the edges in each image by implementing a discrete cosine transform using the discrete cosine transform components comprising the digital data.

29. The system of claim 26, wherein the means for processing determine the total length of the edges by determining differences between selected picture elements in the rows and columns comprising each block and by comparing the differences to a threshold value.

30. The system of claim 29, wherein the means for processing add the edges passing through each row and column of a block to determine a number of the edges disposed within the block, and then sum the number of edges within all of the blocks in the image to determine the total length of the edges in the image.

31. The system of claim 30, wherein the machine instructions executing on the central processor further comprise means for automatically determining a threshold value as a function of differences in gray scale values for picture elements in selected images occurring generally at a midpoint in the coronary angiography procedure.

32. The system of claim 26, wherein the machine instructions executing on the central processor further comprise means for determining the portion of each image that will be processed to select the specific images that depict the coronary arteries during the defined portion of the cardiac cycle.

33. The system of claim 32, wherein the defined portion of the cardiac cycle comprises at least one of an end systole and an end diastole, an image in which the total length of the edges is substantially at a maximum depicting the coronary arteries at the end systole during the cardiac cycle.

34. The system of claim 33, wherein the images in which the total length of the edges is substantially at a minimum depict the coronary arteries at the end diastole during the cardiac cycle.

35. A method for selecting specific frames from an angiography sequence, comprising the steps of:

(a) providing digital data corresponding to a plurality of images of a coronary artery made sequentially in time during the angiography sequence, said digital data indicating gray scale values for a plurality of pixels comprising the images;

(b) using the digital data, estimating a parameter indicative of a separation between branches of the coronary artery in the images over time; and (c) in response to the separation between the branches of the coronary artery that occur during the angiography sequence, selecting the specific frames.

36. The method of claim 35, wherein the specific frames correspond to at least one of two portions of a cardiac cycle, a first portion being generally near an end systole, when the separation between the branches of the coronary artery is substantially at a minimum, and a second portion being generally near an end diastole, when the separation between the branches of the coronary artery is substantially at a maximum.

* * * * *